(12) United States Patent
Gurvich

(10) Patent No.: US 12,330,815 B2
(45) Date of Patent: Jun. 17, 2025

(54) METHOD AND APPARATUS FOR DISINFECTING A VEHICLE INTERIOR

(71) Applicant: AMI Industries, Inc., Colorado Springs, CO (US)

(72) Inventor: Mark R. Gurvich, Middletown, CT (US)

(73) Assignee: AMI Industries, Inc., Colorado Springs, CO (US)

( * ) Notice: Subject to any disclaimer, the term of this patent is extended or adjusted under 35 U.S.C. 154(b) by 907 days.

(21) Appl. No.: 17/342,141

(22) Filed: Jun. 8, 2021

(65) Prior Publication Data
US 2021/0380281 A1    Dec. 9, 2021

Related U.S. Application Data

(60) Provisional application No. 63/036,677, filed on Jun. 9, 2020.

(51) Int. Cl.
*B64F 5/30*    (2017.01)
*A61L 2/06*    (2006.01)
*A61L 2/24*    (2006.01)

(52) U.S. Cl.
CPC .......... *B64F 5/30* (2017.01); *A61L 2/06* (2013.01); *A61L 2/24* (2013.01); *A61L 2202/14* (2013.01);
(Continued)

(58) Field of Classification Search
None
See application file for complete search history.

(56) References Cited

U.S. PATENT DOCUMENTS

| | | | |
|---|---|---|---|
| 2008/0039005 A1* | 2/2008 | Coven | F26B 21/001 34/523 |
| 2012/0255220 A1* | 10/2012 | DeMonte | A01M 1/2094 43/124 |
| 2014/0059796 A1* | 3/2014 | Boodaghians | B64D 11/00 250/455.11 |

(Continued)

FOREIGN PATENT DOCUMENTS

| | | | |
|---|---|---|---|
| CN | 111098673 A | | 5/2020 |
| CN | 111110880 A | * | 5/2020 |
| WO | 2021042802 A1 | | 3/2021 |

OTHER PUBLICATIONS

Beckett et al., Heat as a means for air purification, paper presented at AIEE Winter General Meeting, 1956 (Year: 1956).*

(Continued)

*Primary Examiner* — Holly Kipouros
(74) *Attorney, Agent, or Firm* — Suiter Swantz IP

(57) ABSTRACT

Disclosed are methods and apparatus for disinfecting an interior space in a vehicle such as an aircraft. A method includes determining critical levels of heated air in the interior space of the vehicle required to neutralize effects of at least one predetermined pathogen, providing an apparatus for supplying heated air and positioning the apparatus in the interior space, activating the apparatus to supply the heated air to achieve the determined critical levels of the heated air in the interior space of the vehicle, maintaining the achieved critical levels of the heated air in the interior space for a determined critical time period, and optionally cooling the interior space following completion of the disinfecting process. A disinfecting apparatus may include a heated air generator, blower, controller and optional humidity generator, and may be implemented as a cart for traversing an aisle.

7 Claims, 3 Drawing Sheets

(52) U.S. Cl.
CPC ....... *A61L 2202/15* (2013.01); *A61L 2202/16* (2013.01); *A61L 2202/25* (2013.01)

(56) References Cited

U.S. PATENT DOCUMENTS

| | | | |
|---|---|---|---|
| 2018/0214591 A1* | 8/2018 | Park | A61L 9/14 |
| 2018/0251235 A1* | 9/2018 | Bolton | B64F 5/60 |
| 2019/0366399 A1* | 12/2019 | Prevost | B08B 15/02 |
| 2021/0339712 A1* | 11/2021 | Gutowski | B60H 3/0085 |
| 2022/0118127 A1* | 4/2022 | Brown | A61L 2/24 |
| 2023/0356133 A1* | 11/2023 | Hourani | B60H 3/0608 |
| 2023/0375199 A1* | 11/2023 | Delmiglio | A61L 2/26 |

OTHER PUBLICATIONS

Machine translation of CN 111110880 A provided by Espacenet, original document published May 8, 2020 (Year: 2020).*
Gale et al., Field Evaluation of Whole Airliner Decontamination Technologies for Narrow Body Aircraft, 2008, technical report published by Federal Aviation Administration (Year: 2008).*
Frazy, John S., (2012) Decontamination of Bioaerosols Within Engineering Tolerances of Aircraft Materials (Dissertation), Department of Environmental and Radiological Health Sciences, Colorado State University, pp. 156-220.
Hinds, Allison. (2018). Out with the Mould, in with the New, CBRNe Convergence, Indianapolis Motor Speedway, Indiana, USA, Nov. 6-8, 2017 www.cbrneworld.com /convergence2017.
William T. Greer and Angela Theys, US Air Force Aircraft Decontamination Demonstrations. EPA International Decontamination Conference. May 9, 2018.

* cited by examiner

METHOD AND APPARATUS FOR DISINFECTING A VEHICLE INTERIOR

CROSS-REFERENCE AND INCORPORATION BY REFERENCE

This application claims the benefit of U.S. Provisional Application No. 63/036,677 filed Jun. 9, 2020 and entitled "METHOD AND APPARATUS FOR DISINFECTING A VEHICLE INTERIOR," the disclosure of which is incorporated by reference herein in its entirety.

TECHNICAL FIELD AND BACKGROUND

The present disclosure relates generally to systems, methods and apparatus for disinfecting an interior space in a vehicle.

Current and inevitable future pandemics require mitigation solutions to reduce risks of pathogenic infections, e.g., bacterial and viral transmission. Vehicle interiors, for instance passenger and crew compartments of aircraft, trains, buses, ships and other passenger vessels, are likely environments for transmission due to the close proximity of persons for extended periods of time. Infection in such environments can be especially severe considering certain viruses can persist on interior surfaces such as plastic, composites, metal, and glass, as current studies suggest. Conventional manual disinfection methods for vehicle interiors are expensive, labor intensive, time consuming, and require the use of potentially harmful and/or irritating chemicals, and even more importantly, can be associated with a relatively low probability of complete disinfection.

Accordingly, what is needed is an inexpensive, rapid, expandable, reliable and safe for implementation solution for disinfecting interior surfaces and air in a vehicle interior.

BRIEF SUMMARY

According to a first aspect, the present disclosure provides a method for disinfecting an interior space in a vehicle. The method includes the steps of providing a vehicle having an interior space, providing at least one portable disinfecting apparatus configured to supply heated air, determining critical levels of heated air (e.g., air temperature, humidity) in the interior space of the vehicle required to neutralize effects of at least one predetermined pathogen, such as viruses and/or bacteria, positioning the portable disinfecting apparatus in the interior space of the vehicle, clearing the interior space of all persons, activating the portable disinfecting apparatus to supply the heated air to achieve the determined critical levels of the heated air in the interior space of the vehicle, and maintaining the achieved critical levels of the heated air in the interior space for a determined critical time period to disinfect the interior space.

In some embodiments, the method may further include, subsequent to the step of maintaining the achieved critical levels of the heated air for the determined critical time period, the steps of cooling the interior space of the vehicle and removing the portable disinfecting apparatus(es) from the interior space of the vehicle.

In some embodiments, the step of cooling the interior space of the vehicle may include at least one of exhausting the heated air from the interior space of the vehicle and activating an air conditioning system of the vehicle.

In some embodiments, the portable disinfecting apparatus(es) may include a housing forming an internal area, at least one ambient air inlet, and at least one heated air outlet, a heated air generator positioned in the housing and including a heating element, a blower positioned in the housing configured to flow the heated air generated by the heated air generator out through the at least one heated air outlet, and a controller communicatively coupled to the heated air generator, the controller including a processor configured to activate the heated air generator to achieve the determined critical levels of the heated air in the interior space of the vehicle and maintain the determined critical levels of the heated air for the determined critical time period.

In some embodiments, the portable disinfecting apparatus(es) may further include a humidity generator, wherein the controller is communicatively coupled to the humidity generator and configured to activate the humidity generator to achieve a determined humidity level in the determined critical levels of heated air in the interior space of the vehicle.

In some embodiments, the method may further include the steps of providing at least one portable exhausting apparatus, positioning the portable exhausting apparatus in the interior space of the vehicle remote from the portable disinfecting apparatus(es), and, upon deactivation of the portable disinfecting apparatus(es) after the determined critical time period, activating the portable exhausting apparatus(es) to exhaust heated air from the interior space to cool the interior space.

In some embodiments, the determined critical levels of the heated air may include air temperature and humidity level.

In some embodiments, the vehicle may be an aircraft and the interior space may be a passenger cabin. In other embodiments, the vehicle may be a ground vehicle, for instance a train, bus or ship, or other passenger vehicle.

In some embodiments, the achieved critical levels of the heated air in the interior space of the vehicle may include a relative humidity level less than 10%, and more preferably less than 5%.

According to a second aspect, the present disclosure provides at least one portable disinfecting apparatus, according to the above, for disinfecting an interior space in a vehicle.

In some embodiments, the portable disinfecting apparatus may be implemented as a galley cart configured to traverse along a longitudinal aisle of an aircraft.

According to a third aspect, the present disclosure provides a vehicle interior disinfecting system including at least one portable disinfecting apparatus and at least one portable exhausting apparatus, according to the above, for positioning in an interior space in a vehicle, wherein upon deactivation of the portable disinfecting apparatus(es) after expiration of the determined critical time period, the portable disinfecting apparatus(es) configured to exhaust heated air from the interior space of the vehicle.

In some embodiments, each of the portable disinfecting apparatus and the portable exhausting apparatus may be implemented as a galley cart configured to traverse along an aisle, and wherein the vehicle disinfecting system is configured for disinfecting a passenger cabin of a passenger aircraft between flights or other travels for ground vehicles or ships.

This brief summary is provided solely as an introduction to subject matter that is fully described in the detailed description and illustrated in the drawings. This brief summary should not be considered to describe essential features nor be used to determine the scope of the claims. Moreover, it is to be understood that both the foregoing summary and the following detailed description are exemplary and explanatory only and are not necessarily restrictive of the subject matter claimed. It is to be understood that embodiments of the present disclosure may include one or more or any combination of the foregoing features.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims. In the drawings:

DETAILED DESCRIPTION

Figure 1:
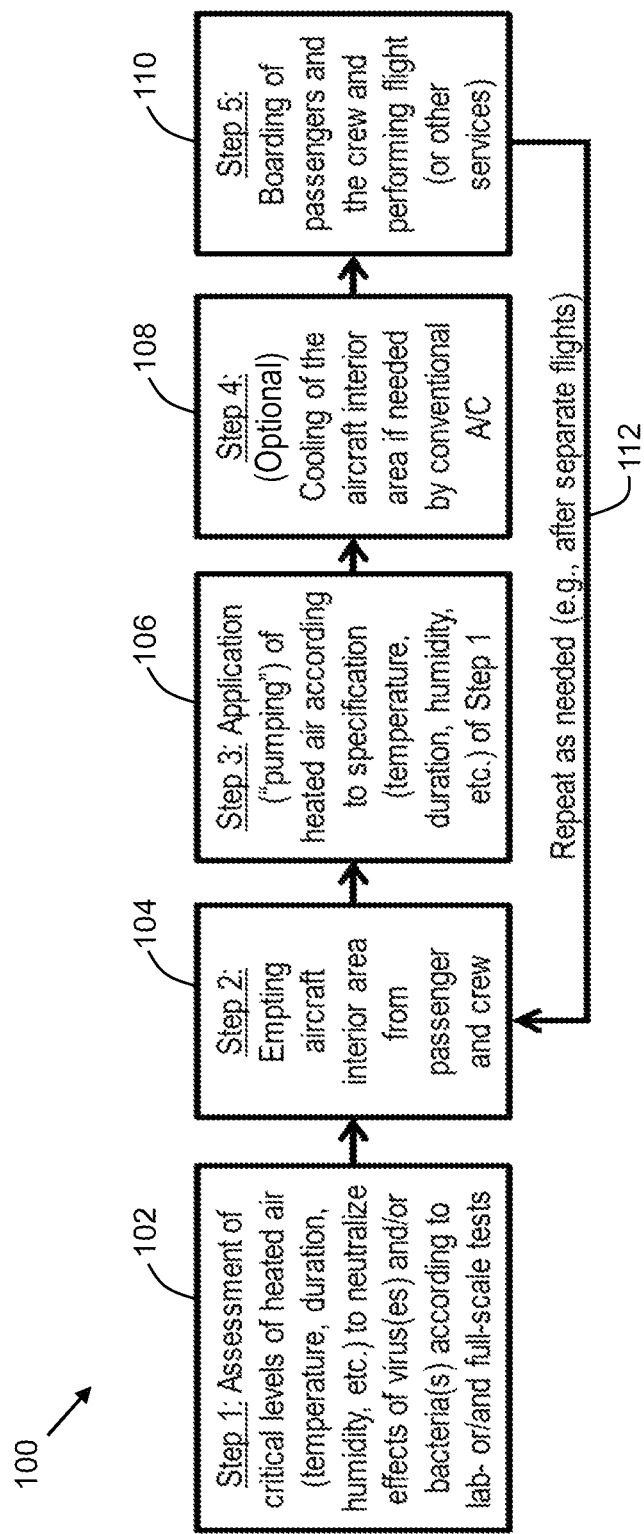
FIG. 1 is a flow diagram illustrating a method for disinfecting an interior space in a vehicle in accordance with an embodiment of the present disclosure.

Before explaining one or more embodiments of the disclosure in detail, it is to be understood that the embodiments are not limited in their application to the details of construction and the arrangement of the components set forth in the following description or illustrated in the drawings. In the following detailed description of embodiments, numerous specific details may be set forth in order to provide a more thorough understanding of the disclosure. However, it will be apparent to one of ordinary skill in the art having the benefit of the instant disclosure that the embodiments disclosed herein may be practiced without some of these specific details. In other instances, well-known features may not be described in detail to avoid unnecessarily complicating the instant disclosure.

As used herein, a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only and should not be construed to limit the disclosure in any way unless expressly stated to the contrary.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" may be employed to describe elements and components of embodiments disclosed herein. This is done merely for convenience and "a" and "an" are intended to include "one" or "at least one," and the singular also includes the plural unless it is obvious that it is meant otherwise.

Finally, as used herein any reference to "one embodiment" or "some embodiments" means that a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination or sub-combination of two or more such features, along with any other features which may not necessarily be expressly described or inherently present in the instant disclosure.

Broadly speaking, the present disclosure is based on the proven sensitivity of pathogens, such as viruses and bacteria, to elevated temperature. For example, studies show that some viruses belonging to the class of coronaviruses become inactive or, at least, exhibit significantly reduced effect after exposure to elevated temperatures for predetermined time periods. In an illustrative embodiment, a method according to present disclosure includes the steps of determining critical levels of heated air (e.g., temperature, duration, humidity, etc.) required to neutralize the effects of pathogens, such as virus(es) and/or bacteria(s), supplying heated air to an interior space of a vehicle, achieving the determined critical air temperature within the interior space, maintaining the achieved critical air temperature for a determined critical time period, and optionally exhausting the heated air from the interior space or cooling the interior space after completion of the disinfection process. The heated air may be supplied utilizing at least one dedicated apparatus introduced into the interior space between uses of the vehicle. Alternatively, the heated air may be supplied via an existing or enhanced capacity heating system of the vehicle.

In another illustrative embodiment, an apparatus according to the present disclosure is configured to supply heated air into the interior space of the vehicle and optionally exhaust heated air from the interior space. In some embodiments, each apparatus may be configured to control at least one of air temperature, humidity level, and duration of operation.

In another illustrative embodiment, a system according to the present disclosure includes at least one apparatus configured to supply heated air positionable within an interior space in a vehicle, and optionally at least one apparatus configured to exhaust heated air positionable within the interior space.

FIG. 1 illustrates a portion of a method 100 for disinfecting an interior space in a vehicle in accordance with an exemplary embodiment of the present disclosure. Broadly speaking, the method generally includes providing a vehicle having an interior space, providing at least one portable disinfecting apparatus as described further below, positioning the portable disinfecting apparatus(es) in the interior space, and activating the portable disinfecting apparatus(es) to achieve determined critical levels of heated air (e.g., air temperature, humidity, duration, etc.) in the interior space. A vehicle according to the present disclosure may include, but is not limited to, aircraft, helicopters, trains, buses, cars, and ships among other conveyances. An interior space according to the present disclosure may include, but is not limited to, passenger cabins, cockpits, crew quarters, lavatories, galleys and baggage compartments, among others.

In Step 102 of the method, critical levels of heated air required to neutralize the effects of virus(es) and/or bacteria(s) are determined. According to the World Health Organization (WHO), temperatures of about 140° F. to about 150° F. (i.e., about 60° C. to about 66° C.) are sufficient to kill or neutralize most viruses, while a temperature of at least 165° F. (i.e., at least about 74° C.) is sufficient to kill or neutralize most bacteria dangerous to humans. The specific threshold temperature or temperature range may depend on the particular pathogen and duration of exposure in heat. For example, some viruses or microbes can be killed or neutralized at lower temperatures with longer exposure times in heat, or conversely, with shorter exposure times at higher temperatures. In some embodiments, determined critical time periods according to the present disclosure may include hours, one hour, thirty minutes, ten minutes, etc., depending on determined critical heated air temperature and particular pathogen(s). In addition to temperature, another critical level of heated air according to the present disclosure may include humidity, defined, for example, as relative humidity (i.e., function of temperature) or absolute humidity (i.e., total amount of water in the air) of the heated air.

In Step 104 of the method, the vehicle including the interior space to be disinfected is emptied of all persons, and optionally sealed. With regard to pressurized aircraft, sufficient sealing may include closing the exit doors. In some embodiments, cabin pressure may be increased by introducing conditioned air to accelerate the disinfecting process.

In Step 106 of the method, the portable disinfecting apparatus(es) positioned in the interior space is activated to achieve the determined critical levels of heated air in the interior space for a determined critical time period. With regard to aircraft, at least one portable disinfecting apparatus may be positioned in the interior space by the flight crew or dedicated cleaning crew between flights. As discussed below, the at least one portable disinfecting apparatus is activated to generate heated air and supply the heated air to the vehicle interior in a diffuse or directed manner. The at least one portable disinfecting apparatus is generally configured to increase the temperature in the vehicle interior to the determined critical temperature, and after achieving the determined critical temperature, maintain at least the determined critical temperature for a determined critical period of time. Each portable disinfecting apparatus may include at least one temperature sensor and a controller or may be communicatively coupled to the same for sensing the air temperature within the vehicle interior and activating or deactivating the portable disinfecting apparatus responsive to the sensed air temperature and programmed operation.

Each portable disinfecting apparatus may optionally be configured to increase or decrease the absolute humidity of the heated air in the interior space depending on the determined critical humidity level. In systems including more than one portable disinfecting apparatus, the apparatuses may be networked and controlled by a master apparatus. In some implementations, the at least one portable disinfecting apparatus may be monitored and controlled remotely via any conventional manner of wireless communication. Apparatus may include any device capable of increasing air temperature and/or modifying humidity level.

In an optional Step 108 of the method, following completion of the disinfecting phase, the interior space of the vehicle may be cooled to accelerate the cycle. In some embodiments, cooling may be achieved using at least one of the air conditioning system of the vehicle and a dedicated portable exhausting device as discussed below.

In Step 110 of the method, upon completion of the disinfecting process and cooling the interior space to ambient temperature or normal cabin temperature, the at least one portable disinfecting apparatus and optional exhausting apparatus are removed from the interior space and persons are permitted to reboard.

In Step 112 of the method, the disinfecting process utilizing the determined critical heated air levels may be repeated after each flight in the case of aircraft, or after each trip in the case of other conveyances. Similarly, the disinfecting process can be repeated after on-ground events involving temporary participation of people such as, for example, maintenance, repair, upgrade, security inspection, etc. In some embodiments, the disinfecting process may be repeated as needed, daily, weekly, monthly, etc.

Figure 2A:
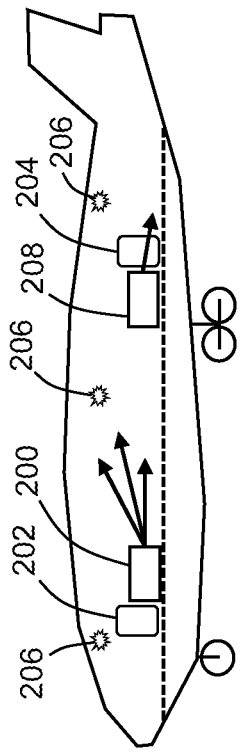
FIG. 2A is a schematic diagram illustrating a system for disinfecting an interior space in a vehicle, for instance an aircraft, in accordance with a first embodiment of the present disclosure.

FIG. 2A illustrates a first embodiment of a disinfecting system for an aircraft shown including a singular portable disinfecting apparatus 200 for supplying heated air. As shown, the apparatus is positioned in the passenger cabin portion of the aircraft proximate the forward exit door 202. In this position, heated air may be supplied at the forward end of the passenger cabin and directed toward the rear of the passenger cabin for complete coverage of the interior space. Upon completion of the disinfecting process, the forward and rear exit doors 202, 204 may be opened to cool the interior space, with or without assistance from the vehicle air conditioning system. In some embodiments, networked temperature and/or humidity sensors 206 positioned strategically throughout the interior space may be configured to sense and report temperature and/or humidity related levels, sensed in the area of the sensors 206, to the apparatus 200 to confirm the critical heated air levels have been achieved in all desired areas of the interior space before initiating the countdown of the critical time period at which the elevated temperature is maintained.

Figure 2B:
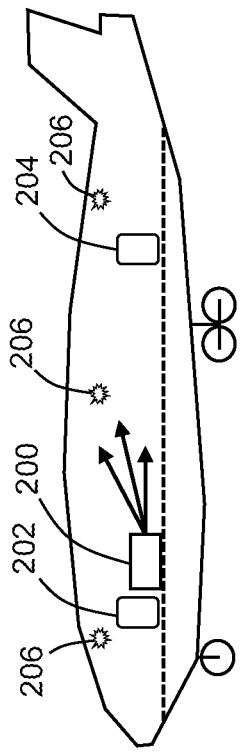
FIG. 2B is a schematic diagram illustrating a system for disinfecting an interior space in an aircraft in accordance with a second embodiment of the present disclosure.

FIG. 2B illustrates a second embodiment of a disinfecting system for an aircraft shown including a singular portable disinfecting apparatus 200 for supplying heated air, and a singular portable exhausting apparatus for exhausting the heated air from the interior space upon completion of the disinfecting cycle. As shown, both apparatuses are positioned in the passenger cabin portion of the aircraft, with the portable disinfecting apparatus 200 positioned proximate the forward exit door 202 and the portable exhausting apparatus positioned proximate the rear exit door 204. In this position, heated air may be supplied at the forward end of the passenger cabin, directed toward the rear of the passenger cabin, and ultimately exhausted out through the rear exit door 204. Temperature and/or humidity sensors 206 may be strategically positioned in the interior space consistent with the first system embodiment.

Figure 2C:
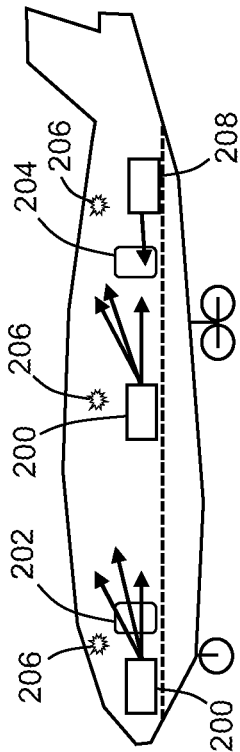
FIG. 2C is a schematic diagram illustrating a system for disinfecting an interior space in an aircraft in accordance with a third embodiment of the present disclosure.

FIG. 2C illustrates a third embodiment of a disinfecting system for an aircraft shown including a singular dual function device 210 configured to both supply heated air during a disinfecting cycle, and exhaust heated air during a cooling cycle. In some embodiments, at the completion of the disinfecting cycle, the heating function of the apparatus may be deactivated while the fan remains activated to direct a flow of ambient air through the vehicle interior toward one or more exits doors 202, 204 to facilitate cooling.

Figure 2D:
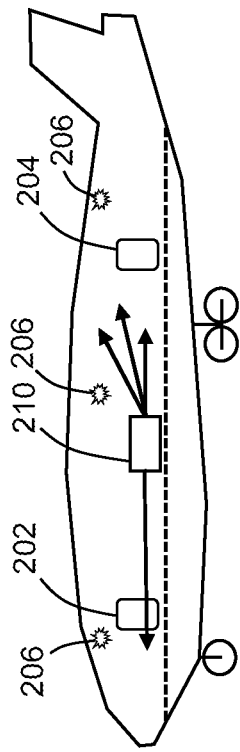
FIG. 2D is a schematic diagram illustrating a system for disinfecting an interior space in an aircraft in accordance with a fourth embodiment of the present disclosure.

FIG. 2D illustrates a fourth embodiment of a disinfecting system for an aircraft shown including a plurality of networked portable disinfecting apparatus 200 configured to supply heated air during a disinfecting cycle, and at least one portable exhausting apparatus 208 configured to exhaust heated air during a cooling cycle. Each portable disinfecting apparatus 200 may be positioned within a predetermined zone in the vehicle interior and the apparatus may be positioned to cooperatively direct the flow of heated air along a predetermined flow path to maximize efficiency of heating and ensure complete sterilization of the interior surfaces. Other embodiments may include variations or combinations of any of the embodiments illustrated in FIGS. 2A-D. Similarly, locations of heating and exhaust apparatuses are shown in FIGS. 2A-D for illustration purposes only and can vary depending on specifics of aircrafts and/or other vehicles.

Each portable disinfecting apparatus may be configured to control at least one of temperature, activation, humidity level, etc. A system controller may control when the disinfection system is activated and deactivated. The apparatus or system may further include motion sensors to monitor motion in the vehicle interior corresponding to the sensed movement of persons, and deactivate the system in the event of sensed motion to enhance the safety of the system. Apparatus can be permanently incorporated into the vehicle dedicated for disinfecting, or part of another vehicle system, or may be temporarily installed, for example, between flights or overnight.

Figure 3:
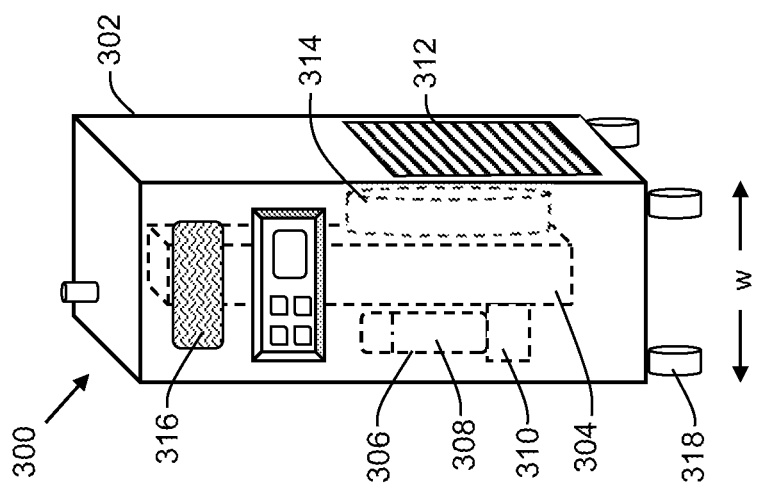
FIG. 3 is a perspective view of a portable disinfecting apparatus in accordance with an embodiment of the present disclosure.

With reference to FIG. 3, in a non-limiting example, a portable disinfecting apparatus 300 according to the present disclosure may include a housing 302 forming an internal area for containing a heated air generator 304 and an optional humidity generator 306 including, for instance, a water tank 308 and atomizer 310. The housing 302 may include a top, a bottom, opposing sides and opposing ends. In some embodiments, a door may be provided on one or more of the opposing sides for accessing the interior portion of the housing 302. The heated air generator 304 includes a heating element, for instance an electric or ceramic heater, for heating ambient air drawn in through at least one vent 312, and a blower 314 that functions to flow heated air out through at least one heated air outlet 316, in a diffuse or directed manner.

In an exemplary implementation, the width dimension (w) of the housing 302 may be comparable to the width dimension of a conventional galley cart to facilitate movement along a longitudinal aircraft aisle while also permitting installation and removal via an aircraft fuselage door. In some embodiments, the overall dimensions of the portable disinfecting apparatus 300 may be comparable to a conventional galley cart to permit stowing in a galley cart bay between uses of the apparatus. The housing 302 may be equipped with latching features for securement in the respective galley cart bay. Wheels or castors 318 provided on the bottom of the housing 302 facilitate movement of the apparatus along the aisle. The housing 302 may or may not be insulated.

Figure 4:
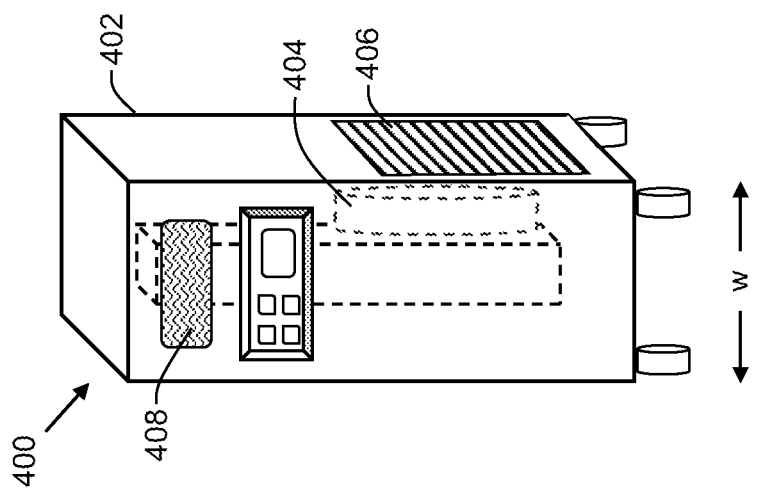
FIG. 4 is a perspective view of an exhausting apparatus in accordance with an embodiment of the present disclosure.

With reference to FIG. 4, in a non-limiting example, a portable exhausting apparatus 400 according to the present disclosure may also include a housing 402 forming an internal area for containing a blower 404 for exhausting heated air, drawn in through an air inlet 406, out through an air outlet 408, in a diffuse or directed manner. As discussed above, the portable disinfecting apparatus may function as an exhausting apparatus by activating the blower with the heated air generator deactivated. Similar to the portable disinfecting apparatus, the portable exhausting apparatus may be implemented dimensioned similar to a galley cart. In some embodiments, one or more of the apparatus may be implemented as an automatic guided vehicle programmed to traverse along an aisle.

Although particular embodiments of the inventive aspects have been illustrated, it is apparent that various modifications of the inventive aspects may be made by those skilled in the art without departing from the scope of the present disclosure.

What is claimed is:

1. A method for disinfecting an interior space in a vehicle, comprising the steps of:
    providing a vehicle having an interior space;
    providing at least one portable disinfecting apparatus configured to supply heated air;
    determining critical levels of heated air in the interior space of the vehicle required to neutralize effects of at least one predetermined pathogen;
    positioning the at least one portable disinfecting apparatus in the interior space of the vehicle;
    activating the at least one portable disinfecting apparatus to supply the heated air to achieve the determined critical levels of the heated air in the interior space of the vehicle;
    maintaining the achieved critical levels of the heated air in the interior space for a determined critical time period to disinfect the interior space;
    providing at least one portable exhausting apparatus;
    positioning the at least one portable exhausting apparatus in the interior space of the vehicle remote from the at least one portable disinfecting apparatus; and
    upon deactivation of the at least one portable disinfecting apparatus after the determined critical time period, activating the at least one portable exhausting apparatus to exhaust the heated and humidified air from the interior space to cool the interior space;
    wherein the at least one portable disinfecting apparatus comprises:
        a housing defining an internal area, at least one ambient air inlet, and at least one heated air outlet;
        a heated air generator positioned in the internal area of the housing and including a heating element;
        a blower positioned in the internal area of the housing, the blower configured to flow heated air generated by the heated air generator out through the at least one heated air outlet; and
        a controller communicatively coupled to the heated air generator, the controller including a processor configured to activate the heated air generator to achieve the determined critical levels of the heated air in the internal area of the vehicle and maintain the determined critical levels of the heated air for the determined critical time period; and
    wherein the vehicle is an aircraft, the interior space is a passenger cabin in the aircraft, and each of the at least one portable disinfecting apparatus and the at least one portable exhausting apparatus is implemented as a galley cart.

2. The method according to claim 1, further comprising, subsequent to the step of maintaining the achieved critical levels of the heated air for the determined critical time period, the steps of:
    cooling the interior space of the vehicle; and
    removing the at least one portable disinfecting apparatus from the interior space of the vehicle.

3. The method according to claim 2, wherein the step of cooling the interior space of the vehicle comprises activating an air conditioning system of the vehicle.

4. The method according to claim 1, wherein the at least one portable disinfecting apparatus further comprises a humidity generator, and wherein the controller is communicatively coupled to the humidity generator and configured to activate the humidity generator to achieve a determined relative humidity level in the heated air.

5. The method according to claim 1, wherein the determined critical levels of the heated air comprise air temperature and humidity level.

6. The method according to claim 1, wherein the achieved critical levels of the heated air in the interior space of the vehicle includes a relative humidity level less than 10%.

7. The method according to claim 1, wherein the achieved critical levels of the heated air in the interior space of the vehicle includes a relative humidity level less than 5%.

\* \* \* \* \*